(12) United States Patent
Schneider et al.

(10) Patent No.: US 8,457,728 B2
(45) Date of Patent: Jun. 4, 2013

(54) AUTOMATIC DETECTION OF PREMATURE VENTRICULAR COMPLEXES FOR HEART RATE TURBULENCE MEASUREMENTS

(75) Inventors: Raphael Schneider, Maastricht (NL); Raja N. Ghanem, Edina, MN (US)

(73) Assignee: Medtronic, Inc., Minneapolis, MN (US)

( * ) Notice: Subject to any disclaimer, the term of this patent is extended or adjusted under 35 U.S.C. 154(b) by 255 days.

(21) Appl. No.: 13/103,157

(22) Filed: May 9, 2011

(65) Prior Publication Data

US 2012/0277608 A1 Nov. 1, 2012

Related U.S. Application Data

(60) Provisional application No. 61/480,044, filed on Apr. 28, 2011.

(51) Int. Cl.
*A61B 5/0456* (2006.01)
(52) U.S. Cl.
USPC ............ 600/521; 600/483; 600/484; 600/509
(58) Field of Classification Search
USPC .................................. 600/483, 484, 509, 521
See application file for complete search history.

(56) References Cited

U.S. PATENT DOCUMENTS

| | | | |
|---|---|---|---|
| 4,336,810 A | 6/1982 | Anderson |
| 4,552,154 A | 11/1985 | Hartlaub |
| 5,097,832 A | 3/1992 | Buchanan |
| 5,271,411 A | 12/1993 | Ripley |
| 5,810,739 A | 9/1998 | Bornzin |
| 6,865,414 B1 | 3/2005 | Levine |
| 7,079,887 B2 | 7/2006 | Burnes et al. |
| 7,181,282 B1 | 2/2007 | Province |
| 7,532,924 B2 | 5/2009 | Ternes |
| 7,783,349 B2 | 8/2010 | Libbus |
| 7,869,870 B1 | 1/2011 | Farazi |
| 2007/0255345 A1 | 11/2007 | Krause |
| 2008/0015651 A1 | 1/2008 | Ettori |
| 2009/0234409 A1 | 9/2009 | Shuros |

*Primary Examiner* — Carl H Layno
*Assistant Examiner* — Jon Eric C Morales
(74) *Attorney, Agent, or Firm* — Michael C. Soldner (57) ABSTRACT

A medical device system and method for monitoring a cardiac signal in a patient senses ventricular R-waves and computes a morphology metric of an R-wave and a corresponding preceding morphology metric of a preceding R-wave. One of a difference and a ratio of the R-wave morphology metric and the preceding R-wave morphology metric is compared to an established detection threshold for discriminating premature ventricular contractions from premature atrial contractions. A cardiac signal measurement is computed from the sensed R-waves in response to detecting a premature ventricular comparison based on the comparison.

24 Claims, 9 Drawing Sheets

AUTOMATIC DETECTION OF PREMATURE VENTRICULAR COMPLEXES FOR HEART RATE TURBULENCE MEASUREMENTS

REFERENCE TO RELATED APPLICATIONS

The present non-provisional U.S. Patent Application claims the benefit of U.S. Patent Application 61/480,044, filed provisionally on Apr. 28, 2011, and entitled "DISTINGUISHING PREMATURE CONTRACTIONS IN A MEDICAL DEVICE", incorporated by herein by reference in it's entirety.

TECHNICAL FIELD

The present disclosure relates generally to cardiac monitoring systems and, in particular, to a method and apparatus for detecting premature ventricular contractions for use in measuring heart rate turbulence.

BACKGROUND

Patients suffering from heart failure can experience severe symptoms leading to hospitalization as their heart failure worsens. It is desirable to prevent hospitalization and worsening heart failure symptoms by managing medications and other heart failure therapies, such as cardiac resynchronization therapy (CRT). However, clinicians are challenged in detecting a worsening state of heart failure patient before the patient becomes overtly symptomatic and hospitalization is required. A need remains for medical devices and methods for ambulatory monitoring of heart failure patients which allows early detection of a worsening heart failure condition.

DETAILED DESCRIPTION

In the following description, references are made to illustrative embodiments. It is understood that other embodiments may be utilized without departing from the scope of the disclosure. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

An impaired autonomic nervous system (ANS) is associated with higher mortality and hospitalization risk in patients. Heart rate turbulence (HRT) is a physiological response of the sinus node to a premature ventricular contraction (PVC). HRT can be used as a measure of the health of the ANS. A PVC causes a brief disturbance of heart rate and arterial blood pressure. A PVC is a ventricular depolarization, also referred to as a ventricular ectopic beat, arising from the ventricular myocardium, rather than arising from the sinoatrial node and being conducted normally from the atria to the ventricles through the heart's natural conduction system.

When a PVC occurs, the heart typically does not have ample time to fill with blood prior to the premature beat, thus resulting in reduced arterial blood pressure and blood flow. In a healthy person, this change in blood pressure typically stimulates baroreceptors, which are nerve endings in the vasculature that are sensitive to changes in blood pressure. When the baroreceptors are stimulated, a neural reflex affects the heart and vasculature to increase heart rate and blood pressure in an attempt to restore the body to its normal state. Until the normal pressure can be restored, however, oscillations in the patient's heart rate is frequently observed due to the changes in cardiac output originating with the PVC beat. If the patient is in good health, the response to changes in cardiac output and arterial pressure is relatively large and the heart recovers relatively quickly. If the patient has an impaired ANS diminishing the arterial baroreflex, heart rate oscillations may be depressed. Accordingly, the duration and magnitude of heart rate turbulence (HRT) following a heart beat perturbation can be a good indicator of the health of the ANS of the patient. In particular, measuring HRT following a PVC is believed to be useful in identifying patients at risk for congestive heart failure (CHF), CHF decompensation, sudden cardiac death, and other forms of heart disease.

A PVC can be observed as a short ventricular cycle, i.e. the interval between two consecutive R-waves, with no intervening atrial beat. For HRT calculation it is important that only PVCs are used and not premature atrial contractions (PACs) because the response of the sinus rhythm after a PAC produces different results. The different response following a PAC, if measured and included with measurements associated with a true PVC, would confound HRT measurements. A PAC can be conducted to the ventricles and appear like a short ventricular cycle, potentially being detected as a PVC when PVC detection is based on intervals measured between R-waves. In a dual chamber device having both atrial and ventricular sensing electrodes or when using multi-lead ECG signals, PVCs can be readily identified by a shortened ventricular cycle length without an intervening atrial depolarization signal, i.e. a P-wave.

In a cardiac monitoring device that relies on a single ECG lead, subcutaneous electrodes, or a single chamber device having electrodes located only in a ventricular chamber, it can be difficult to differentiate PACs and PVCs based on the absence of a P-wave during a short ventricular cycle because the P-wave signal is of very low amplitude or absent. Furthermore, the available processing power in a small implantable device, such as an implantable ECG recorder or hemodynamic monitor, may be limited precluding highly complex signal analysis methods. Automatic and reliable identification of PVCs originating in the ventricles, i.e. ventricular ectopic beats, for HRT assessment that requires only a single ECG lead or EGM signal without requiring high processing burden is needed.

In addition to subcutaneous or external cardiac monitors, the relationship between HRT and cardiac health can be beneficially exploited in other implantable medical devices (IMDs) such as pacemakers, implantable cardioverter-defibrillators (ICDs), an automatic external defibrillator (AED) or heart monitor and the like. According to various embodiments, an implantable medical device (IMD) detects PVCs and monitors HRT resulting from a PVC to determine an indication of the patient's cardiac health. The perturbation may be naturally occurring in the patient. HRT measurements made by the IMD can be used for enhanced monitoring, diagnosis and/or therapeutic functions in response to the measured turbulence. For example, the IMD may store diagnostic data in a memory, activate an alarm to the patient if medical attention is potentially warranted, or the like. In further embodiments, the IMD administers or adjusts an appropriate therapy or other response when such treatment or adjustment to the treatment is needed. As used herein, the term "response" is intended to broadly encompass any type of medical response, alarm, report, telemetered data or the like (including storage of data within the IMD), as well as any of the various therapies that may be provided by the IMD to the patient. In a further embodiment, HRT may be used to determine optimal settings for a pacemaker, or for optimal delivery of a pharmaceutical or other therapy.

Figure 1:
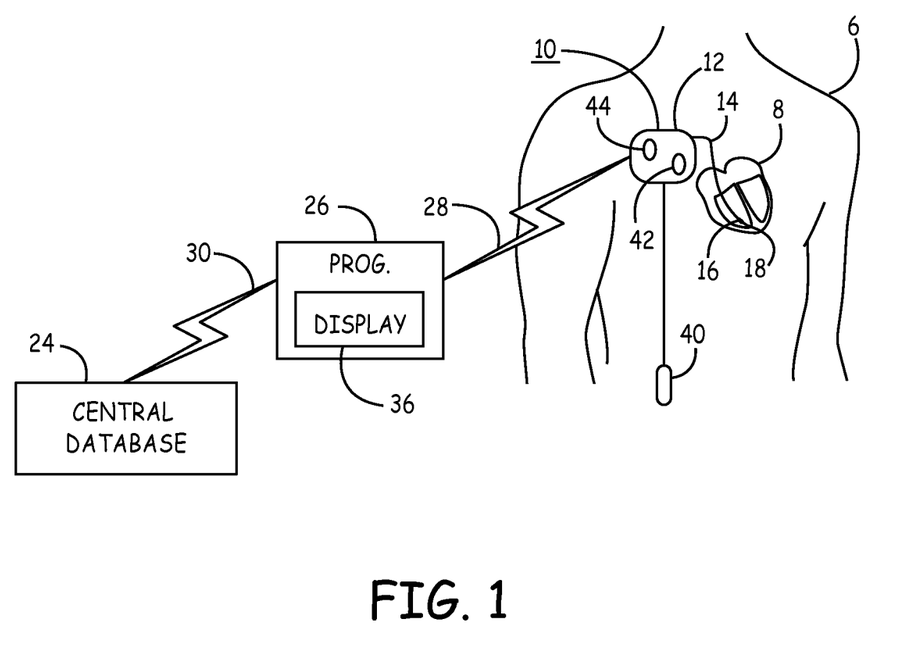
FIG. 1 is a schematic diagram of an implantable medical device (IMD) optionally coupled to a lead positioned within a heart in a patient's body.

FIG. 1 is a schematic diagram of an IMD 10 optionally coupled to a lead 14 positioned within a heart 8 in a patient's body 6. IMD 10 may correspond to a variety of implantable medical devices including an ECG monitor, cardiac pacemaker, implantable cardioverter defibrillator (ICD), implantable hemodynamic monitor, a drug pump, a neurostimulator or the like. IMD 10 may or may not be provided with therapy delivery capabilities. When provided with therapy delivery capabilities, IMD 10 may be coupled to additional leads and/or catheters operatively positioned relative to the patient's heart 8 or other body tissues for deploying stimulating/sensing electrodes, physiological sensors, and/or drug delivery ports. While lead 14 is shown carrying sense/pace electrodes 16 and 18 positioned within the right ventricle of the patient's heart in the illustrative embodiment, it is recognized that lead 14 may be configured to extend transvenously into other heart chambers or blood vessels or subcutaneously away from IMD 10 to other body locations for positioning any number of electrodes and/or physiological sensors in a desired location.

In one embodiment, IMD 10 corresponds to an implantable cardiac signal monitor capable of at least sensing an ECG or intracardiac EGM signal using an intracardiac lead 14 and/or subcutaneous electrodes 42 and 44 incorporated in the housing 12 of IMD 10. Subcutaneous electrodes may additionally or alternatively be carried by a lead. IMD 10 receives the ECG and/or EGM signals, collectively referred to herein as "cardiac electrical signals" or simply "cardiac signals".

Housing 12 encloses circuitry (not shown in FIG. 1) included in IMD 10 for controlling and performing device functions and processing sensed signals as described herein. Cardiac signals may be stored and/or analyzed by IMD 10 for diagnostic or prognostic purposes. Cardiac arrhythmias, heart rate, premature contractions, and other events may be detected and corresponding data may be stored by IMD 10.

In particular and as further described herein, IMD 10 will detect PVCs and evaluate cardiac signals subsequent to the disturbance associated with a PVC for computing metrics of HRT. HRT metrics are then available to a clinician for diagnosis and prognosis of various heart-related conditions.

IMD 10 is capable of bidirectional communication with an external device 26 via bidirectional telemetry link 28. Device 26 may be embodied as a programmer, typically located in a hospital or clinic, used to program the operating mode and various operational variables of IMD 10 and interrogate IMD 10 to retrieve data acquired and stored by IMD 10. Device 26 may alternatively be embodied as a home monitor used for remote patient monitoring for retrieving data from the IMD 10. Data stored and retrieved from IMD 10 may include data related to IMD function determined through automated self-diagnostic tests as well as physiological data acquired by IMD 10 including HRT data.

External device 26 is further shown in communication with a central database 24 via communication link 30, which may be a wireless or hardwired link. Programming data and interrogation data may be transmitted via link 30. Central database 24 may be a centralized computer, Internet-based or other networked database used by a clinician for remote monitoring and management of patient 6. An example of a remote patient management system in which tissue oxygenation monitoring may be incorporated for monitoring heart failure patients is generally described in commonly-assigned U.S. Pat. No. 6,599,250 (Webb, et al.), hereby incorporated herein by reference in its entirety. It is recognized that other external devices, such as other physiological monitoring devices or other types of programming devices, may be used in conjunction with IMD 10 and incorporate portions of the methods described herein.

The methods described herein for analyzing cardiac signals to determine HRT metrics may be implemented in IMD 10 and the results of data analysis transmitted to external device 26 upon an interrogation request and optionally on to central database 24. IMD receives a cardiac signal, detects PVCs, computes HRT metrics and stores the metrics for transmission to external device 26. Alternatively, raw cardiac signal data may be transmitted from IMD 10 to external device 26 with the data analysis performed by external device 26 and/or central database 24. In still other embodiments, the signal analysis may be performed in a distributed manner across the IMD 10, external device 26, and/or central database 24. For example, IMD 10 may detect PVCs and transmit only cardiac signal segments containing a valid PVC for HRT analysis by external device 26 or central database 24.

Figure 2:
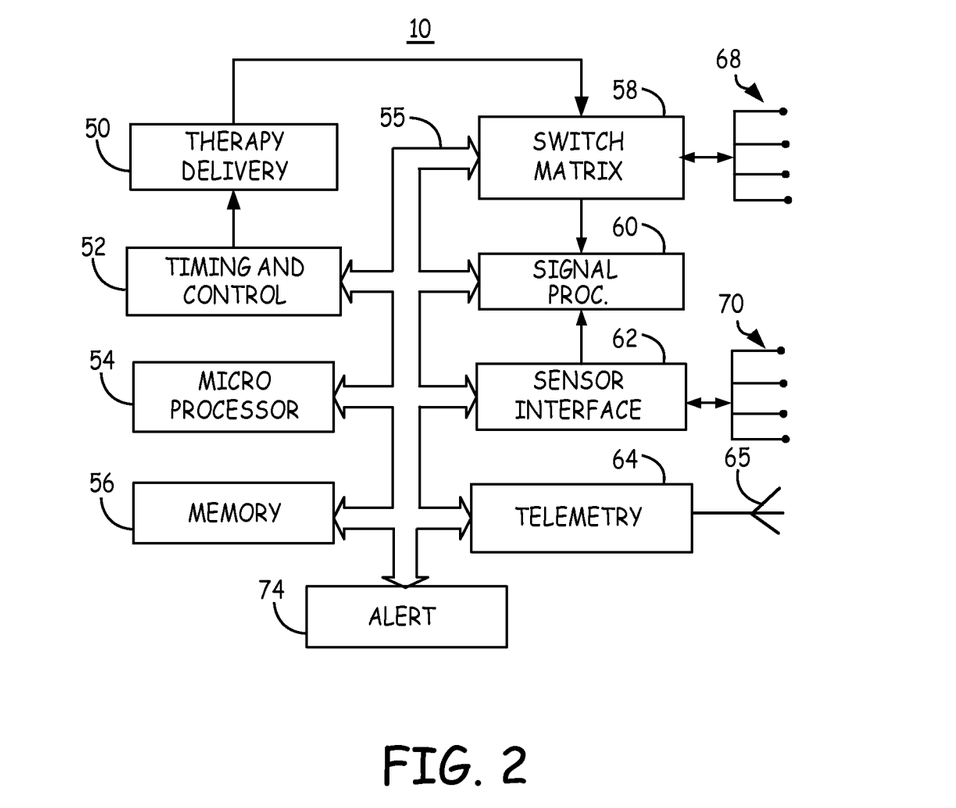
FIG. 2 is a functional block diagram of one embodiment of the IMD shown in FIG. 1.

FIG. 2 is a functional block diagram of one embodiment of IMD 10. IMD 10 generally includes timing and control circuitry 52 and an operating system that may employ microprocessor 54 or a digital state machine for timing sensing and therapy delivery functions (when present) in accordance with a programmed operating mode. Microprocessor 54 and associated memory 56 are coupled to the various components of IMD 10 via a data/address bus 55.

IMD 10 may include therapy delivery module 50 for delivering a therapy under the control of microprocessor 54 in response to determining a need for therapy, e.g., based on sensed physiological signals. Therapy delivery module 50 may provide drug delivery therapies or electrical stimulation therapies, including neurostimulation or cardiac pacing, cardiac resynchronization therapy, or anti-arrhythmia therapies. Therapies are delivered by module 50 under the control of timing and control circuitry 52.

Therapy delivery module 50 may be coupled to two or more electrodes 68 via an optional switch matrix 58 for delivering an electrical stimulation therapy such as cardiac pacing or neurostimulation. Electrodes 68 may correspond to any of the electrodes 16, 18, 42 and 44 shown in FIG. 1.

Electrodes 68 are also used for receiving cardiac electrical signals through any unipolar or bipolar sensing configuration. Cardiac electrical signals are monitored for diagnostic or prognostic purposes, managing a patient condition, and may be used for determining when an automatically-delivered therapy is needed and controlling the timing and delivery of the therapy. Signal processor 60 receives cardiac signals and includes sense amplifiers and may include other signal conditioning circuitry and an analog-to-digital converter. Cardiac electrical signals received from electrodes 68, which may be intracardiac EGM signals, far field EGM signals, or subcutaneous ECG signals, are used for detecting PVCs and determining HRT metrics.

IMD 10 may be coupled to one or more sensors 70 of physiological signals other than cardiac electrical signals. Physiological sensors may include a pressure sensor, activity sensor, oxygen sensor or the like. Sensor signals are received by sensor interface 62, which may provide initial amplification, filtering, rectification, or other signal conditioning. Sensor signals are used by signal processor 60 and/or microprocessor 54 for detecting physiological events or conditions.

The operating system includes associated memory 56 for storing operating algorithms and control parameter values that are used by microprocessor 54. The memory 56 may also be used for storing data compiled from sensed cardiac signals and/or relating to device operating history for telemetry out on receipt of a retrieval or interrogation instruction. Microprocessor 54 may respond to cardiac signals by altering a therapy, triggering data analysis and storage, or triggering alert 74 to generate an alert signal to the patient or a clinician that a condition has been detected that may require medical intervention. Data relating to physiological signal processing may be stored in memory 56 for later retrieval. For example, PVC detection may trigger a HRT analysis and data storage. When PVC detections, a HRT metric or trend thereof reaches a predetermined threshold, an alert signal may be generated by alert module 74 in the form of an audible sound, vibration, transmittable message or other notification.

Figure 3:
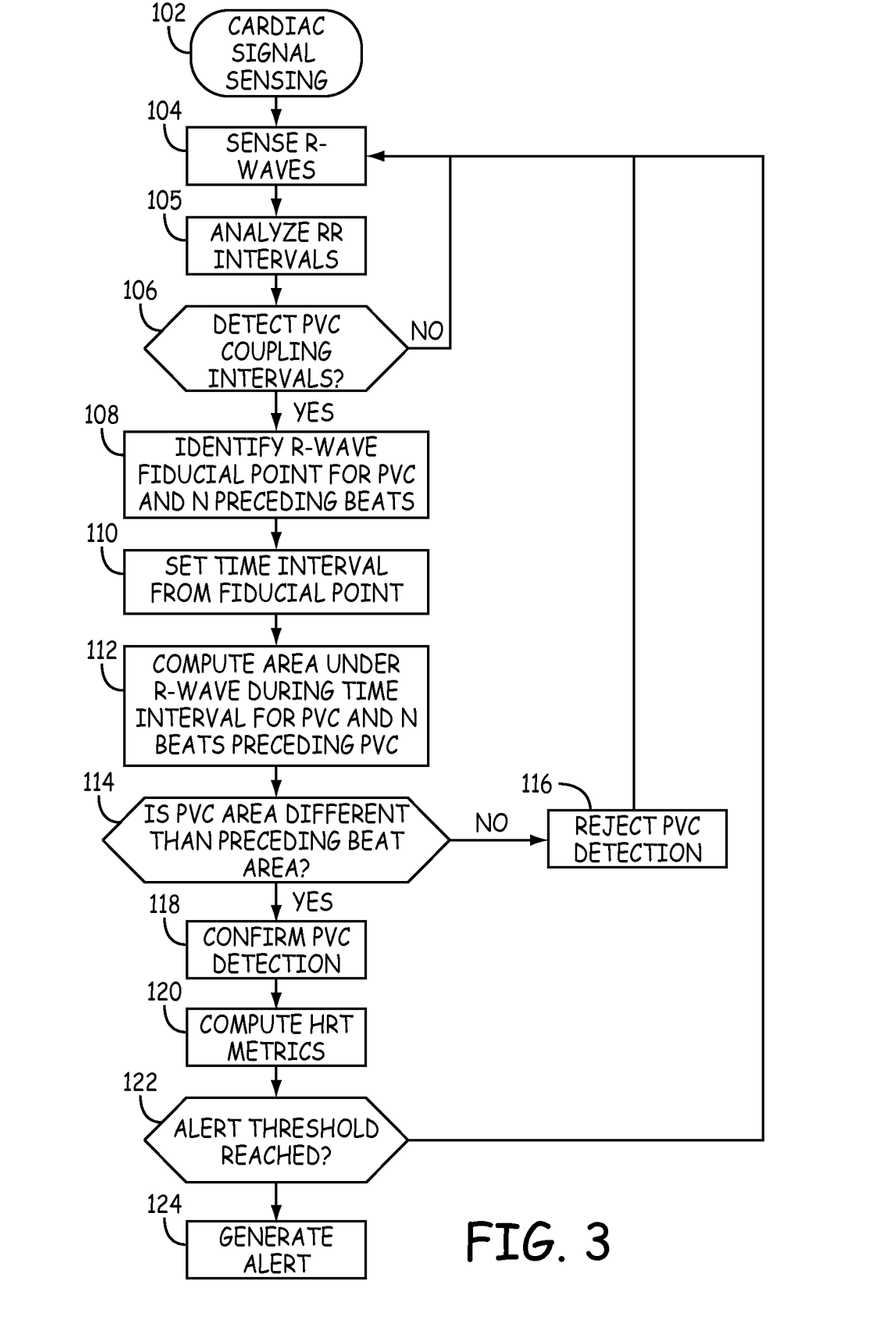
FIG. 3 is a flow chart of a method for monitoring HRT in a patient.

FIG. 3 is a flow chart 100 of a method for monitoring HRT in a patient. Flow chart 100 and other flow charts presented herein are intended to illustrate the functional operation of the device, and should not be construed as reflective of a specific form of software or hardware necessary to practice the methods described. It is believed that the particular form of software will be determined primarily by the particular system architecture employed in the device and by the particular detection and therapy delivery methodologies employed by the device. Providing software to accomplish the described functionality in the context of any modern IMD, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 102, cardiac signal sensing is performed using one or more selected electrode pairs. At block 104, R-waves are sensed from the cardiac signal. R-wave sensing may be performed according to any method implemented in the IMD. Typically, an automatically adjusting threshold is applied to the cardiac signal for sensing R-waves as generally described in U.S. Pat. No. 5,117,824 (Keimel, et al.), hereby incorporated herein by reference in its entirety. At block 105, intervals between consecutively sensed R-waves, i.e. RR intervals, are analyzed to determine if an RR interval corresponding to a PVC coupling interval is detected as determined at decision block 106. Criteria for detecting a PVC coupling interval may vary between embodiments. One method for detecting a PVC coupling interval is described in greater detail in conjunction with FIG. 4. Generally, a PVC coupling interval is detected as an interval that is shorter than at least one or more preceding RR intervals. Additionally or alternatively, one or more subsequent RR intervals may be compared to a given RR interval for detecting a PVC coupling interval.

If a PVC coupling interval is detected, as determined at decision block 106, the process advances to block 108 to identify an R-wave fiducial point for each of the PVC QRS complex and a selected number N preceding sensed R-waves. As long as a PVC coupling interval is not detected, the process continues to sense R-waves (block 104) and analyze RR intervals (block 105). The fiducial point identified at block 108 may correspond to the R-wave amplitude at the time of R-wave detection, a maximum peak R-wave amplitude (of a rectified or non-rectified signal), a minimum R-wave peak, a maximum slope, or other selected point along the QRS complex.

At block 110, at least one time interval is established beginning or ending at the fiducial point and extending a predetermined time from the fiducial point for each of the PVC and N preceding beats. The area under the R-wave during the established time interval is computed at block 112 for the PVC and the N preceding beats. The predetermined time may be in the range of approximately 25 ms to approximately 100 ms or more an may vary between embodiments. The time interval may generally be defined to maintain the time interval within an expected QRS complex width. Alternatively, the time interval may be defined to extend beyond an expected normal QRS complex width (i.e. beyond a beginning or end of a normal QRS width), to allow a wider QRS width associated with a PVC to be detected based on a change in area under the R-wave signal during the established time interval.

The computed area under the R-wave during the established time interval for the suspected PVC detected based on the detected PVC coupling interval is compared to the area(s) computed for the N preceding beats at block 114. A representative area for the N preceding beats may be determined for comparison to the area computed for the suspected PVC. For example an average, median, nth maximum area or other statistical measure may be determined for the N preceding beats. A difference or ratio of the suspected PVC area may then be computed and compared to a predefined PVC detection threshold. Alternatively, a difference or ratio of the suspected PVC area and each of the N preceding beats may be computed and the computed differences or ratios combined in a summation, average, or other representative number are compared to a PVC detection threshold. It is understood that many specific implementations may be conceived for detecting a clinically significant difference between an area computed for a suspected PVC and an area computed for one or more preceding beats.

If the PVC area is not different (negative result at decision block 114), the suspected PVC is rejected at block 116. In other words the suspected PVC based on a detected PVC coupling interval is rejected as not being a PVC. The PVC coupling interval detected at block 106 may be associated with a PAC, oversensing of a T-wave or other non-cardiac related signal noise. If the PVC detection is rejected at block 116, the process returns to block 104 to continue sensing R-waves and analyzing RR intervals for detecting a PVC coupling interval. HRT metrics are not computed.

If the PVC detection threshold criteria applied to the computed areas is satisfied at decision block 114, a PVC detection is confirmed at block 118. PVC detection triggers an analysis of RR intervals preceding and subsequent to the detected PVC and computation of HRT metrics at block 120. It is noted that HRT metrics such as Turbulence Onset and Turbulence Slope are usually computed using RR intervals measured in response to multiple PVCs, not just one PVC detection. If a HRT metric reaches an alert threshold at block 122, an alert is generated at block 124 to notify the patient and/or clinician of the detected condition and allow the clinician to assess the patient's condition and take any appropriate intervention. If an alert threshold is not reached, patient monitoring continues by returning to block 104.

It is recognized that in addition to or alternatively to generating an alert at block 124 the IMD may be configured to provide other responses to the HRT analysis. An IMD capable of delivering a cardiac therapy may be triggered to adjust the therapy based on the HRT metric. Furthermore, whenever HRT metrics are computed at block 120, it is understood that if the metrics are being computed by a processor incorporated in the IMD, the HRT metrics are stored for transmission to an external device as described in conjunction with FIG. 1. The digitized cardiac signal or data associated with the PVC detection, preceding beats, and/or subsequent beats may be stored along with HRT metrics for review by a clinician. In an another embodiment, confirmed detection of the PVC at block 118 causes storage of a cardiac signal strip including preceding and subsequent beats needed for HRT analysis to be performed by an external device after transmission of the cardiac signal strip to the external device.

Figure 4:
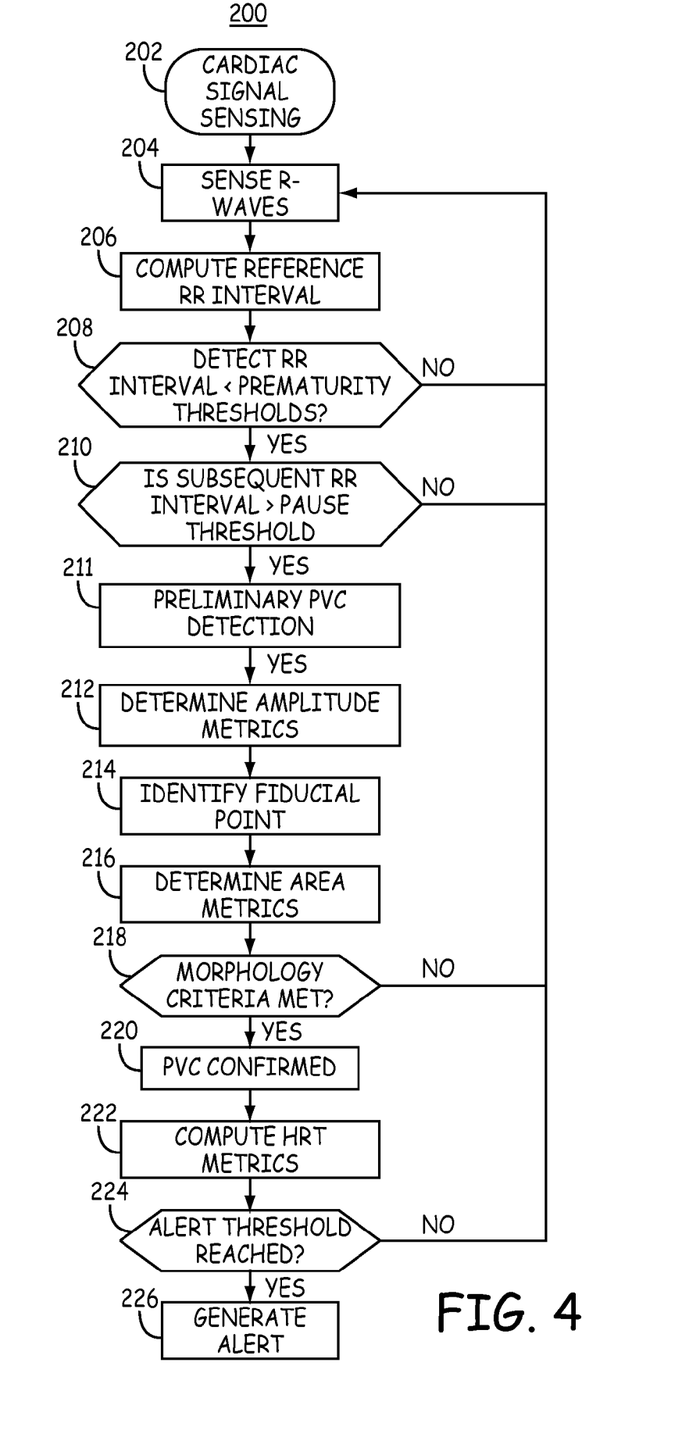
FIG. 4 is a flow chart of a method for monitoring HRT according to an alternative embodiment.

FIG. 4 is a flow chart 200 of a method for monitoring HRT according to an alternative embodiment. At block 202, cardiac signal sensing is initiated. R-waves are sensed at block 204 according to an R-wave detection method implemented in the IMD. At block 206, a reference RR interval is computed. The reference RR interval is computed to provide a baseline RR interval used in identifying an unexpectedly short RR interval associated with a possible PVC coupling interval. A reference RR interval may be computed as a running average or a median of a most recent number of RR intervals. For example, in one embodiment, the reference RR interval is computed as the median of the most recent 11 RR intervals.

At block 208, a current RR interval is compared to a prematurity threshold for determining whether a PVC coupling interval is detected. The prematurity threshold is defined as a percentage of the reference RR interval. In one embodiment, a prematurity of 80%, i.e. an RR interval that is less than 80% of the reference RR interval, is detected as potential PVC coupling interval.

If an RR interval less than the prematurity threshold is detected at block 208, the immediately subsequent RR interval is compared to a pause threshold at decision block 210. A PVC is normally followed by a long RR interval, often referred to as the "compensatory pause". A pause threshold for detecting the compensatory pause following a potential PVC is defined as a percentage of the reference RR interval in one embodiment. For example, if the RR interval immediately following a potential PVC coupling interval is greater than 120% of the reference RR interval, a preliminary PVC detection is made at block 211.

If RR intervals do not meet the timing-related criteria for detecting a PVC applied at decision steps 208 and 210, the process continues to sense R-waves at block 204 and measure RR intervals at block 206. If these timing-related criteria are satisfied at blocks 208 and 210, morphology-related metrics of the suspected PVC are determined at blocks 212 and 214. The morphology-related metrics are used to either confirm or reject the preliminary PVC detection.

Figure 5A:
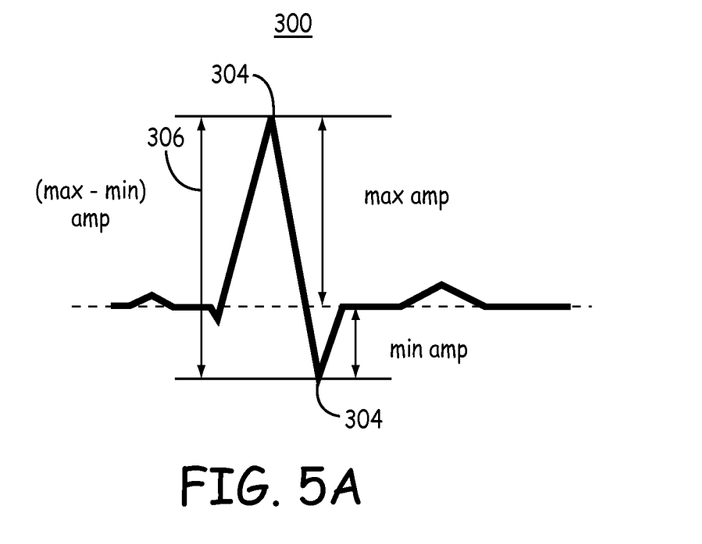
FIG. 5A is a representative R-wave showing amplitude metrics that may be determined for use in confirming a premature ventricular contraction (PVC).

At block 212, amplitude metrics are determined. FIG. 5A is a representative R-wave 300 showing amplitude metrics that may be determined for use in confirming a PVC. In one embodiment, a maximum amplitude 302, a minimum amplitude 304, and a max-min difference 306 are determined.

Figure 5B:
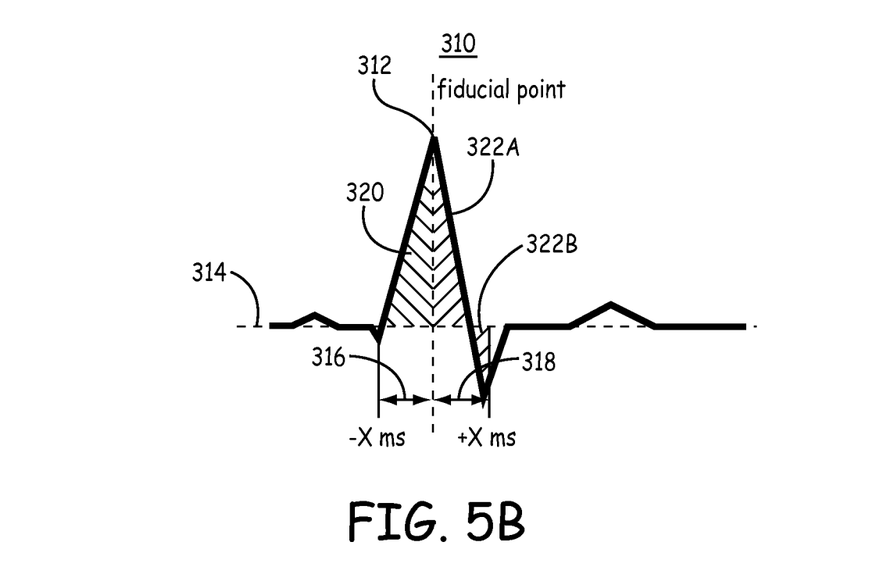
FIG. 5B is a representative R-wave showing area metrics that may be determined for use in confirming a PVC.

At block 214, a fiducial point is identified and area metrics are computed at block 216 using the fiducial point. FIG. 5B is a representative R-wave 310 showing area metrics that may be determined for use in confirming a PVC. A fiducial point 312 is identified for establishing time intervals over which an area defined between the R-wave and a baseline 314 is computed. In the example shown, the maximum R-wave peak is identified as the fiducial point 312. In an alternative embodiment, the point at which the R-wave crosses a sensing threshold for R-wave detection is identified as the fiducial point. In still other embodiments, a fiducial point may be identified as a peak slope or baseline crossing.

After identifying the fiducial point, a time interval 316 is defined relative to fiducial point 312. Time interval 316 ends at the time of the fiducial point 312 and extends a predetermined time interval, X ms, earlier than the fiducial point. A second time interval 318 is defined beginning at the fiducial point 312 and ending a predetermined time interval, X ms, later than the fiducial point.

A first area 320 under the R-wave 310 is computed over the interval 316 ending at the fiducial point 312. A second area 322, collectively 322A and 322B, defined by R-wave 310 and baseline 314 is computed over time interval 318. In some embodiments, the absolute values of the areas 322A and 322B are summed or R-wave 310 may be rectified such that both areas 322A and 322B are positive-going areas and are summed to obtain a total area corresponding to time interval 318. In other embodiments, the negative-going area 322B may be subtracted from the positive-going area 322A to obtain a net positive area over the interval 318 corresponding to the difference between 322A and 322B.

In FIG. 5B, the time intervals 316 and 318 are shown to extend for equal time intervals of X ms. In alternative embodiments, two distinct time intervals are defined for establishing a first time interval ending at the fiducial point 312 and a second time interval beginning at the fiducial point 312. The second time interval may extend for a different amount of time from the fiducial point than the first time interval. The time intervals 316 and 318 may each extend between 0 ms and 100 ms or more from the fiducial point, for example, approximately 25 ms, approximately 50 ms, or approximately 100 ms, or more from the fiducial point 312. In one embodiment, a fiducial point is identified as the maximum positive-going slope of R-wave 310. A first time interval is defined extending approximately 50 ms earlier than the maximum positive-going slope and a second time interval is defined extending approximately 100 ms. In another embodiment, the first and second areas extending 50 ms and 100 ms before and after a maximum peak of a rectified R-wave are determined.

Area metrics that are computed for detecting a PVC may include a first area 320 defined by a time interval 316 that ends at the fiducial point 312, a second area 322 that begins at fiducial point 312, a sum of areas 320 and 322, a ratio of areas 320 and 322, or a difference of areas 320 and 322. While two areas 320 and 322 are shown and described, it is recognized that multiple areas computed over respective time intervals defined using one or more fiducial points may be used individually or in various combinations to determine an area metric for use in detecting a PVC.

Referring again to FIG. 4, R-wave area metrics are computed at block 216 using the fiducial point and defined time intervals relative to the fiducial point. At decision block 218, the area metrics and the amplitude metrics are compared to morphology criteria for detecting a PVC. A threshold for each of the metrics is predetermined to distinguish between a PVC and a PAC or other noise or artifact.

In one embodiment, the area metrics determined at block 216 are determined for both the suspected PVC beat and one or more immediately preceding beats. In this way, the generation and storage of a predefined morphology template for detecting a PVC is not needed. A ratio or difference between the area metric for the suspected PVC beat and the corresponding area metric for the immediately preceding beat is determined and compared to a PVC detection threshold at block 218.

For example, in one embodiment, the area under the R-wave over a 50 ms interval ending at the maximum peak of the R-wave is computed for the suspected PVC and the immediately preceding beat. The difference between these areas is determined and compared to a predetermined threshold found to distinguish PVCs and PACs with a high degree of certainty. In another embodiment, a sum of a first area extending for 50 ms preceding the maximum R-wave peak and a second area extending for 100 ms following the maximum R-wave peak is determined as a summed area for each of the suspected PVC beat and the immediately preceding beat. The ratio of the summed areas is compared to a predetermined threshold that distinguishes PVCs from PACs.

The thresholds used to compare to R-wave amplitude and area metrics for confirming a PVC detection may be established based on clinical data from a population of patients. Alternatively, thresholds may be individualized for a particular patient through analysis of naturally occurring and/or pacing-induced PACs and PVCs.

If the morphology-related criteria are not met at decision block 218, the preliminary PVC detection is rejected and the process returns to block 204 to continue sensing R-waves. If morphology-related criteria are satisfied at block 218, the preliminary PVC detection is confirmed at block 220. The valid PVC detection triggers computation of HRT metrics at block 222. HRT data is stored for later retrieval and review by a clinician. If a HRT metric reaches a response threshold, the IMD may respond accordingly. For example, if an alert threshold is reached as determined at block 224, a patient or clinician alert is generated at block 226 or another response is provided.

It is understood that although the preliminary PVC detection is described as being satisfied in Block 211 of FIG. 4 when intervals requirements are met, and therefore the timing-related criteria applied at Block 208 and 210 are shown to be determined prior to the morphology-related criteria of Blocks 212-218, the order of detection between the time-related and the morphology-related criteria could be reversed, so that the preliminary PVC detection could be based on the morphology-related criteria, and followed by the time-related criteria if the morphology-related criteria are satisfied.

Figure 6:
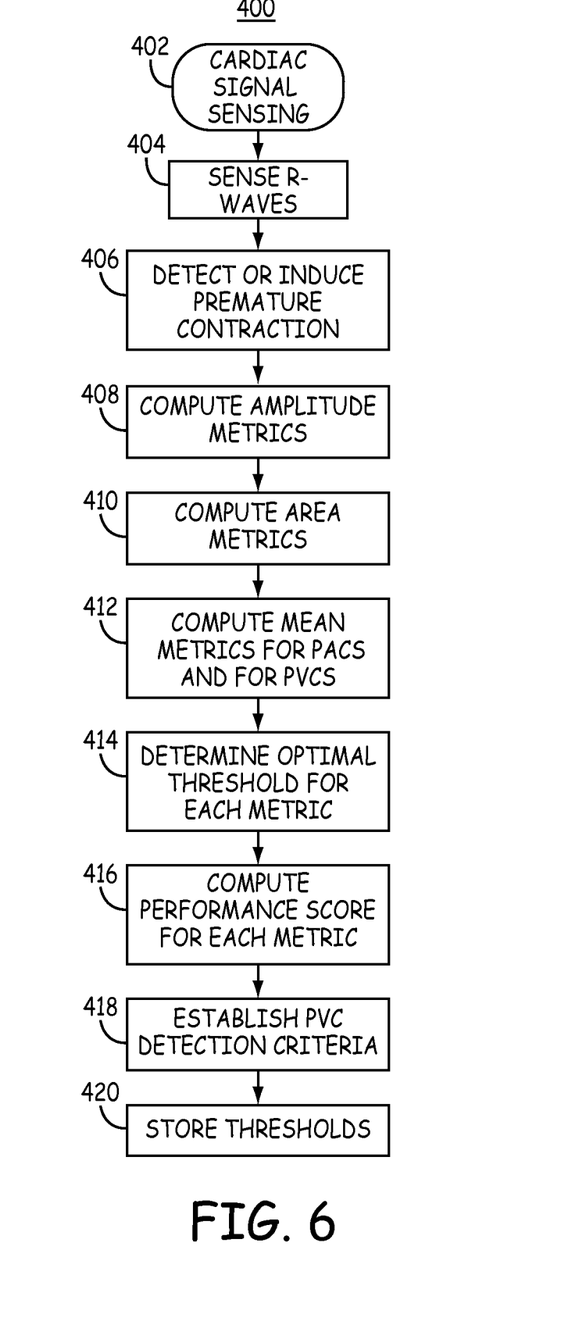
FIG. 6 is a flow chart of a method for establishing morphology-related metrics and thresholds for positively identifying PVCs during HRT monitoring.

FIG. 6 is a flow chart 400 of a method for establishing morphology-related metrics and thresholds for positively identifying PVCs during HRT monitoring. The particular amplitude or area metric that distinguishes PACs and PVCs with the highest degree of confidence may vary between patients due to the particular lead and electrode configuration used and other factors. As such, an analysis may be performed to compare the sensitivity, specificity and confidence of multiple amplitude and/or area metrics in correctly distinguishing PACs and PVCs for a given patient or patient population. The process shown in flow chart 400, therefore, may be performed using cardiac signals acquired from an individual patient or from a population of patients. Cardiac signals may be acquired over a period of time to collect a number of spontaneously occurring PACs and PVCs. Additionally or alternatively, cardiac signals may be acquired during an office visit in which PACs and PVCs are induced by pacing pulses.

The statistical computations described in the following description may be too high of a computational burden to be practically implemented in an implantable device. In some embodiments, the process shown in flow chart 400 is implemented in an IMD system including an external processor, such as the system in FIG. 1. Statistical analysis and establishment of PVC detection criteria may be performed by the external processor and then stored or programmed in the IMD, or a small wearable external device, for use in ambulatory patient monitoring.

At block 404, R-waves are sensed. At block 406, a number of premature contractions are sensed and/or induced, including both PACs and PVCs. Spontaneous premature contractions are detected from the cardiac signal based on RR interval measurements or based on a known premature pacing pulse. As described previously, spontaneous premature beats may be detected based on RR intervals being less than a prematurity threshold followed by RR intervals being greater than a pause threshold.

For each premature beat, one or more amplitude metrics are computed at block 408 and one or more area metrics are computed at block 410. The amplitude metrics may include the maximum peak, the minimum peak and the peak-to-peak amplitude as shown in FIG. 5A. Computation of the area metrics involves first identifying a fiducial point as described previously then establishing time intervals beginning and/or ending at the fiducial point and computing an area bounded by the R-wave and the baseline over each of the established time intervals. The time intervals may extend, for example, 50 ms earlier, 100 ms earlier, 50 ms later and 100 ms later than the fiducial point and/or other selected time intervals. Area metrics may include an area over a single time interval or summed areas occurring over an earlier (ending at the fiducial point) and later (beginning at the fiducial point) time interval.

At block 412 the premature contractions are distinguished as PVCs and PACs to allow computation of mean values for each amplitude and area metric separately for PACs and for PVCs. Distinguishing PVCs and PACs may be performed manually by an expert or automatically based on an atrial signal if one is available for determining if a P-wave precedes an R-wave occurring at a premature coupling interval. When PACs and PVCs are pacing induced, the mean metrics are computed separately for PACs and PVCs according to the known premature pacing pulses.

At block 414, the mean values for each metric are used for determining an optimal threshold for each metric that separates the PACs from the PVCs with a high degree of confidence. In one embodiment, a threshold for each amplitude and area metric is determined that results in the maximum Chi Square test statistic for separating PACs from PVCs for that metric. Each metric and corresponding optimal threshold are then evaluated at block 416 to determine a minimized set of area and/or amplitude metrics for use in positive PVC identification. This minimized set of discriminatory morphology metrics allows discrimination of PVCs from PACs (or other noise or artifact) using a ventricular or subcutaneous cardiac signal only.

In one embodiment a performance score is computed at block 416 for scoring the performance of each metric in positively identifying PVCs with a high degree of confidence. The score may be a weighted combination of statistical measures of the metric threshold performance in separating PVCs and PACs. For example, the Chi Square test statistic, PVC sensitivity as a percentage of all premature beats, PVC specificity as a percentage of all premature beats, the positive predictive power as a percentage, and the negative predictive power as a percentage may all be calculated for an optimal threshold identified at block 414 for a given metric.

For each statistical measure, the best performing thresholds are identified and given points according to a point value system established to rate the best performing metrics. For example, the best performing metric based on a given statistical measure is identified and given 3 points; the second best performing threshold based on the same statistical measure is identified and given 2 points, and the third best performing threshold is identified and given 1 point. More specifically, the amplitude metric (e.g., max, min or peak-to-peak) having the highest Chi Square test statistic may be given 3 points and the amplitude metric having the lowest Chi Square test statistic may be given 1 point. Similar point assignments are made for the amplitude metrics for each of the other statistical indicators, i.e. sensitivity, specificity, positive predictive power and negative predictive power. Each area metric is likewise awarded points based on the best performing to the worst performing metric according to each individual statistical measure.

The received points for a given metric threshold are summed to determine an overall performance score for the corresponding metric. The performance score represents a combination of the individual statistical measures for a given amplitude or area metric. The amplitude and area metrics may be assessed separately to identify a best performing amplitude metric and a best performing area metric. Alternatively, the amplitude and area metrics may be grouped and awarded points to determine the overall best performing metrics.

At block 418, PVC detection criteria are established based on the performance scores computed at block 416. In one embodiment, the best performing amplitude metric and the best performing area metric are identified. The optimal thresholds identified for these best performing metrics are stored at block 420 establishing PVC detection criteria for a given patient or population of patients. These established detection criteria are used during patient monitoring for detecting PVCs for triggering a HRT monitoring algorithm.

The criteria established at block 418 may require that an amplitude metric and an area metric for a suspected PVC each meet a respective threshold requirement in order to confirm a time-interval based PVC detection. Alternatively, a best amplitude metric and a best area metric may be combined and a combined threshold identified and stored at block 420. For example, the best amplitude metric and the best area metric may be combined in a weighted combination. A corresponding threshold applied to the combined morphology metric would be computed or scaled appropriately for application to the weighted combination for reliable discrimination of PVCs.

In one embodiment, amplitude and area metrics are computed as ratios of a morphology metric measured from the suspected PVC beat and the corresponding metric measured from the immediately preceding beat. The best performing amplitude metric and the best performing area metric can easily be combined in a single metric when both metrics are determined as ratios. In a specific example, a ratio of the maximum R-wave amplitude of a suspected PVC and the maximum R-wave amplitude of the immediately preceding beat may be identified as a best performing amplitude metric. A ratio of a summed area for the PVC beat and the summed area for the immediately preceding beat may be identified as the best performing area metric, where the summed area is the combined area under the R-wave over a first time interval preceding the R-wave maximum peak by 50 ms and a second time interval extending from the R-wave maximum peak for 100 ms. In an empirical study performed by the inventors, these metrics were found to be the best performing metrics with an optimal threshold of approximately 40% for the summed area ratio and approximately 20% for the amplitude ratio. As such, a threshold criterion established at block 418 may require that a sum of the summed area ratio and twice the amplitude ratio must be greater than approximately 80% (40% plus twice 20%) to positively detect a PVC.

In other embodiments, a single amplitude or area parameter identified as having the highest performance score may be identified at block 416. The PVC detection criterion established at block 418 requires the single metric to meet the optimal threshold determined at block 414 for positively detecting a PVC.

Figure 7:
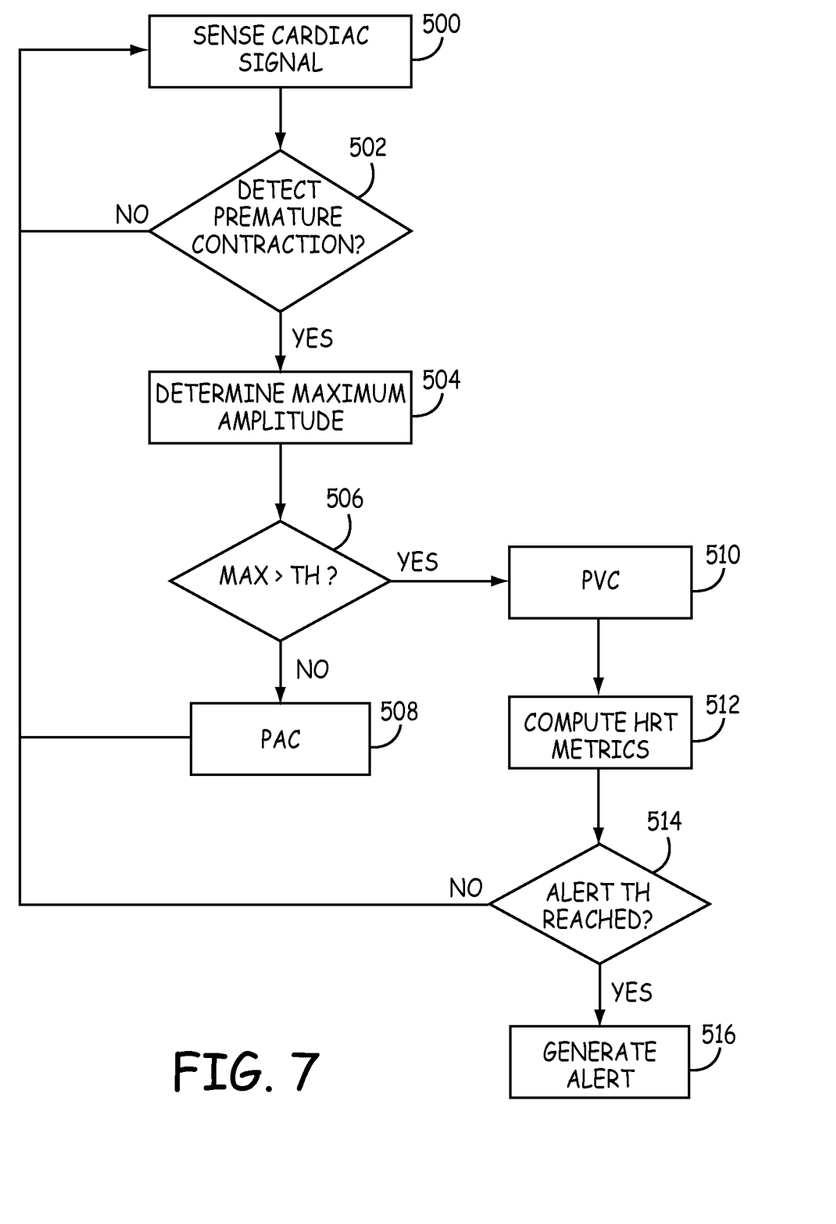
FIG. 7 is a flowchart of a method of distinguishing premature contractions as being one of a premature atrial contraction and a premature ventricular contraction, according to an embodiment of the disclosure.

FIG. 7 is a flowchart of a method of distinguishing premature contractions as being one of a premature atrial contraction and a premature ventricular contraction, according to an embodiment of the disclosure. As illustrated in FIG. 7, according to one embodiment, during distinguishing of a premature contraction as being one of a PVC and a PAC, R-waves are sensed from a sensed cardiac signal, Block 500, and intervals between consecutively sensed R-waves, i.e., RR intervals, are analyzed to determine if an RR interval corresponding to a premature contraction is detected, Block 502. In order to detect the occurrence of a premature contraction, for example, the device determines whether a detected RR interval is less than a predetermined threshold. The premature contraction threshold may be a fixed value, or may be determined based on one or more preceding RR intervals and/or one or more subsequent RR intervals.

If a premature contraction is not detected, the device continues sensing cardiac signals, Block 500. If a premature contraction is detected, a metric of the detected RR-interval is determined and compared to a premature contraction threshold. For example, a maximum amplitude of the R-wave associated with the detected RR interval corresponding to the premature contraction is determined, Block 504, and a determination is made as to whether the maximum amplitude of the R-wave is greater than a predetermined threshold, Block 506. According to one embodiment, for example, the predetermined threshold corresponds to a percentage increase of the maximum amplitude from the amplitude of one or more RR-intervals occurring prior to the RR-interval associated with the detecting of the premature contraction, such as 20 percent for example.

If the maximum interval is less than or equal to the predetermined threshold, i.e., less than or equal to a 20 percent increase from one or more previous RR-intervals, the premature contraction is identified as being associated with a PAC, Block 508, and the device continues sensing cardiac signals, Block 500. If the maximum interval is determined to be greater than the predetermined threshold, i.e., greater than a 20 percent increase from one or more previous RR-intervals, the premature contraction is identified as being associated with a PVC, Block 510.

According to an embodiment of the disclosure, if the premature contraction is determined to be associated with a PVC, heart rate turbulence metrics may be determined and stored, Block 512, and once an alert threshold associated with the determined PVCs is reached, Yes in Block 514, a patient or clinician alert is generated, Block 516, as described above. If the alert threshold has not been reached, No in Block 514, and the device continues sensing cardiac signals, Block 500.

Figure 8:
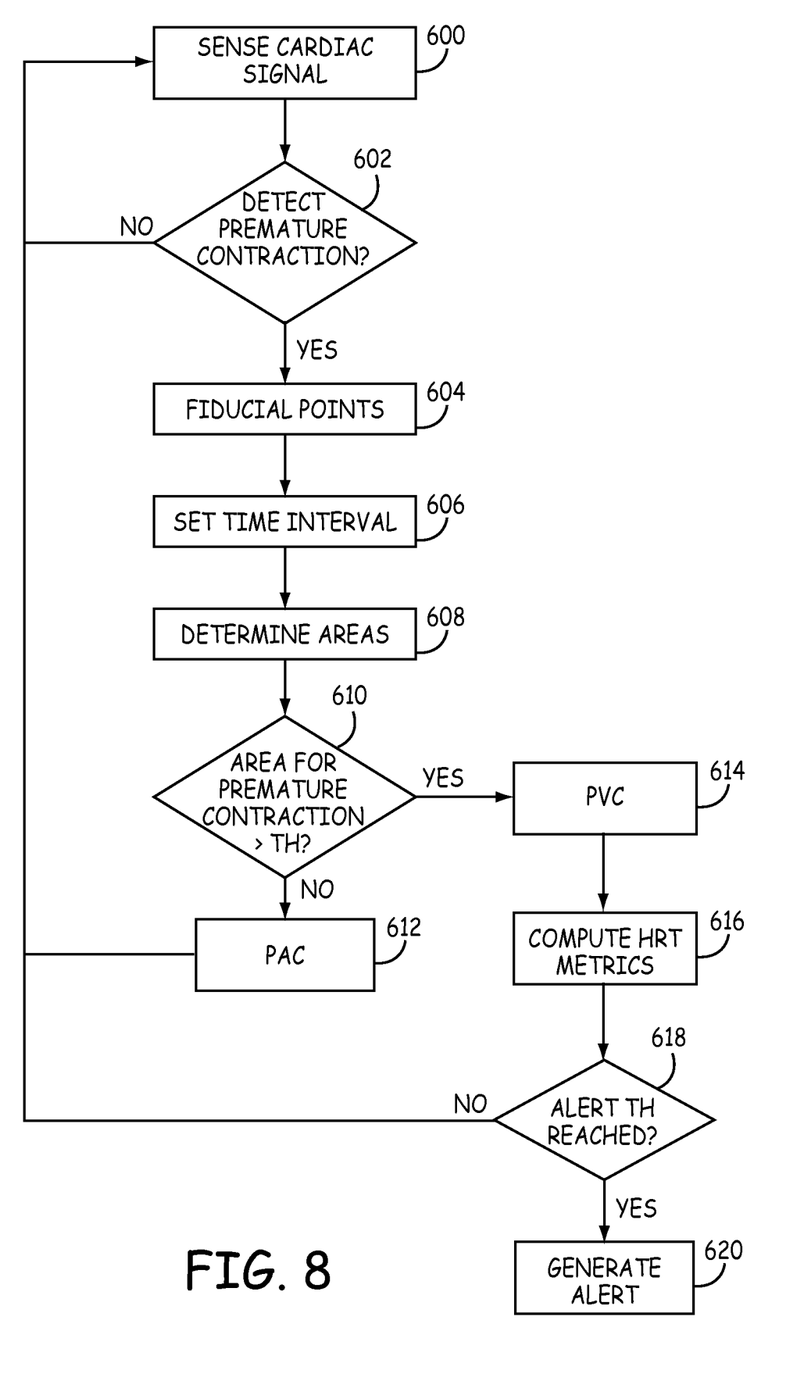
FIG. 8 is a flowchart of a method of distinguishing premature contractions as being one of a premature atrial contraction and a premature ventricular contraction, according to an embodiment of the disclosure.

FIG. 8 is a flowchart of a method of distinguishing premature contractions as being one of a premature atrial contraction and a premature ventricular contraction, according to an embodiment of the disclosure. As illustrated in FIG. 8, according to one embodiment, during distinguishing of a premature contraction as being one of a PVC or a PAC, R-waves are sensed from a sensed cardiac signal, Block 600, and intervals between consecutively sensed R-waves, i.e., RR intervals, are analyzed to determine if an RR interval corresponding to a premature contraction is detected, Block 602. In order to detect the occurrence of a premature contraction, for example, the device determines whether a detected RR interval is less than a predetermined threshold. The premature contraction threshold may be a fixed value, or may be determined based on one or more preceding RR intervals and/or one or more subsequent RR intervals.

If a premature contraction is not detected, the device continues sensing cardiac signals, Block 600. If a premature contraction is detected, a metric of the detected RR-interval is determined and compared to a premature contraction threshold. For example, the device determines an R-wave fiducial point for both an R-wave of the detected RR interval associated with the premature contraction being determined and a selected number N of preceding sensed R-waves, or beats, Block 604. A time interval is established beginning and/or ending at the determined fiducial point and extending a predetermined time from the fiducial point both the R-wave of the detected RR interval associated with the determined premature contraction and the selected number N of preceding sensed R-waves, Block 606. According to one embodiment, for example, the time interval is set as being 50 ms prior to the fiducial point and 100 ms after the fiducial point.

The area under the R-wave fiducial points during the time interval for both the R-wave of the detected RR interval associated with the premature contraction being determined and the selected number N of preceding sensed R-waves is then determined, Block 608, and a determination is made as to whether the area determined for the R-wave of the detected RR interval associated with the determined premature contraction is greater than a predetermined area threshold, Block 610. According to one embodiment, for example, the predetermined area threshold corresponds to a percentage increase or decrease of the area associated with the R-wave of the detected RR interval associated with the determined premature contraction from the N preceding sensed R-waves, such as 39 percent for example.

According to one embodiment, the area under the R-wave of the detected RR interval associated with the premature interval is compared with the area under the R-wave of the immediately preceding beat. In another embodiment, the areas of a predetermined number N of prior beats may be combined into a single metric, such as an average, for example, or a comparison is made between the percent increases to X out of Y beats, for example.

If the area determined for the R-wave of the detected RR interval associated with the determined premature contraction is less than or equal to the predetermined threshold, i.e., less than or equal to a 39 percent increase or decrease from the N previous R-waves, the premature contraction is identified as being associated with a PAC, Block 612, and the device continues sensing cardiac signals, Block 600. If the area determined for the R-wave of the detected RR interval associated with the determined premature contraction is determined to be greater than the predetermined threshold, i.e., greater than a 39 percent increase or decrease from one or more previous RR-intervals, the premature contraction is identified as being associated with a PVC, Block 614.

According to an embodiment of the disclosure, if the R-wave of the detected RR interval associated with the determined premature contraction is determined to be associated with a PVC, heart rate turbulence metrics may be determined and stored, Block 616, and once an alert threshold associated with the determined PVCs is reached, Yes in Block 618, a patient or clinician alert is generated, Block 620, as described above. If the alert threshold has not been reached, No in Block 618, and the device continues sensing cardiac signals, Block 600.

Figure 9:
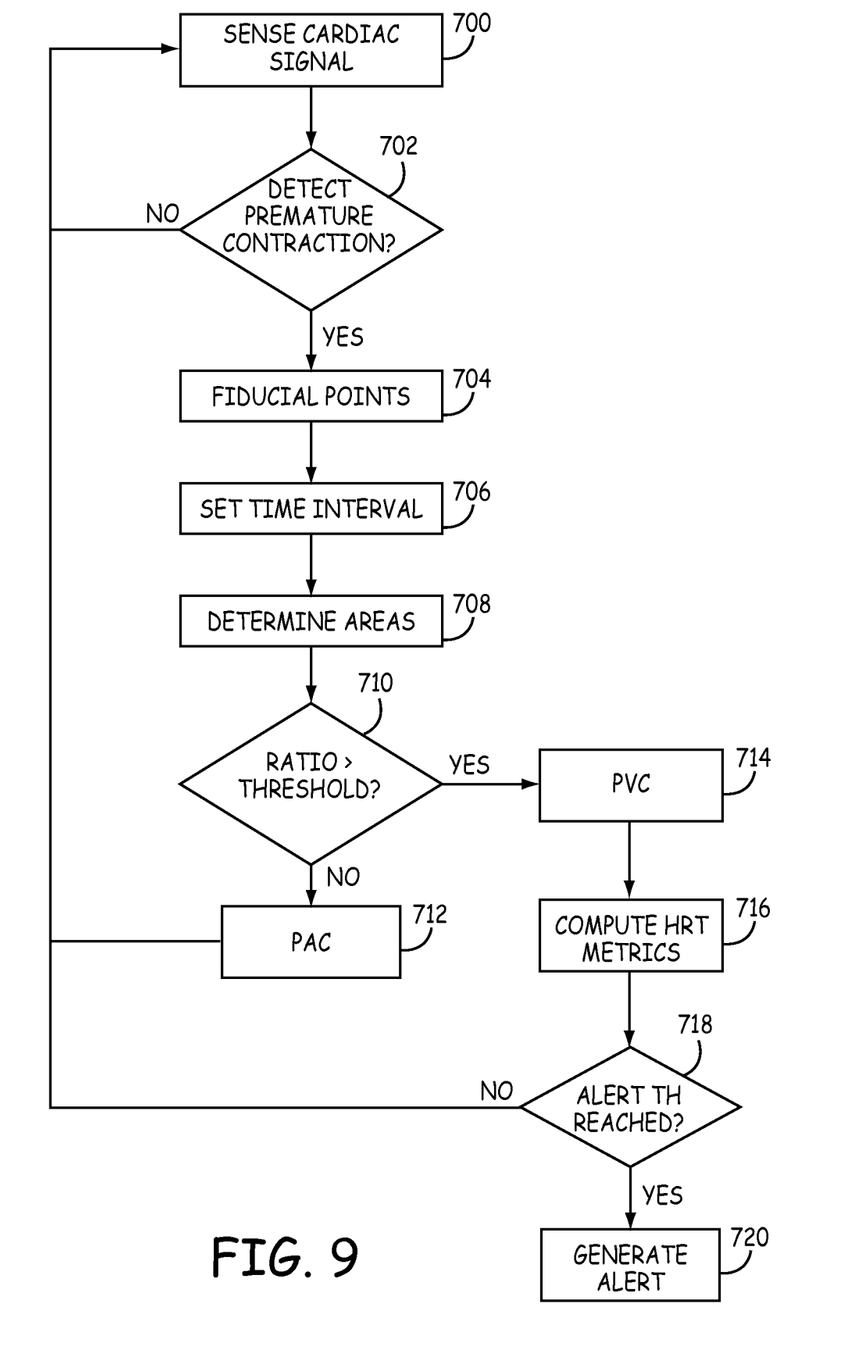
FIG. 9 is a flowchart of a method of distinguishing premature contractions as being one of a premature atrial contraction and a premature ventricular contraction, according to an embodiment of the disclosure.

FIG. 9 is a flowchart of a method of distinguishing premature contractions as being one of a premature atrial contraction and a premature ventricular contraction, according to an embodiment of the disclosure. As illustrated in FIG. 9, according to one embodiment, during distinguishing of a premature contraction as being one of a PVC and a PAC, R-waves are sensed from a sensed cardiac signal, Block 700, and intervals between consecutively sensed R-waves, i.e., RR intervals, are analyzed to determine if an RR interval corresponding to a premature contraction is detected, Block 702. In order to detect the occurrence of a premature contraction, for example, the device determines whether a detected RR interval is less than a predetermined threshold. The premature contraction threshold may be a fixed value, or may be determined based on one or more preceding RR intervals and/or one or more subsequent RR intervals.

If a premature contraction is not detected, the device continues sensing cardiac signals, Block 700. Once a premature contraction is detected, a metric of the detected RR-interval is determined and compared to a premature contraction threshold. For example, the device determines an R-wave fiducial point for both an R-wave of the detected RR interval associated with the premature contraction being determined and a selected number N of preceding sensed R-waves, or beats, Block 704. A time interval is established beginning and/or ending at the determined fiducial point and extending a predetermined time from the fiducial point for each of the R-wave of the detected RR interval associated with the determined premature contraction and the selected number N of preceding sensed R-waves, Block 706. According to one embodiment, for example, the time interval is set as being 50 ms prior to the fiducial point and 100 ms after the fiducial point.

The area under the R-wave fiducial points is determined for both the R-wave of the detected RR interval associated with the premature contraction being determined and the area associated with a selected number N of preceding sensed R-waves is determined, Block 708. The determination of the area corresponding to the selected number N of preceding R-waves is identified as an area associated with a normal beat. A determination is made as to whether an increase or decrease of a ratio of the area of the R-wave associated with the premature contraction being determined and the area associated with a normal beat is greater than a predetermined threshold, Block 710. According to one embodiment, for example, the predetermined threshold corresponds to a percentage increase or decrease of a ratio of the area of the R-wave associated with the premature contraction being determined and the area associated with a normal beat, such as 55 percent for example.

If the ratio of the area of the R-wave associated with the premature contraction being determined and the area associated with a normal beat is not greater than the area threshold, the premature contraction is identified as being associated with a PAC, Block 712, and the device continues sensing cardiac signals, Block 700. If the ratio of the area of the R-wave associated with the premature contraction being determined and the area associated with a normal beat is greater than the area threshold, the premature contraction is identified as being associated with a PVC, Block 714.

According to an embodiment of the disclosure, if the premature contraction is identified as being associated with a PVC, heart rate turbulence metrics may be determined and stored, Block 716, a determination is made as to whether the determined heart rate turbulence reaches an alert threshold, Block 718. If the alert threshold has not been reached, NO in Block 718, the device continues sensing cardiac signals, Block 700. If the determined heart rate turbulence is greater than the alert threshold, Yes in Block 718, a patient or clinician alert is generated, Block 720, as described above. According to one embodiment, the alert threshold corresponds to determining a combination of heart rate turbulence parameters, such as turbulence onset and turbulence slope, for example, so that the alert threshold is a determination of whether none, one or both of the parameters are determined to be abnormal. In particular, the turbulence onset may be considered abnormal if there is a positive change in heart rate turbulence, and turbulence slope may be considered abnormal if the turbulence slope is less than 2.5 ms/RR-interval.

While methods described herein relate to detecting PVCs for use in HRT monitoring, it is recognized that the methods described may be implemented in any patient monitoring algorithm that requires reliable PVC detection. Apparatus and methods have been presented in the foregoing description with reference to specific embodiments. It is appreciated that various modifications to the referenced embodiments may be made without departing from the scope of the disclosure as set forth in the following claims.

The invention claimed is:

1. A method for monitoring a cardiac signal in a patient, comprising:
    establishing a detection threshold requirement for discriminating premature ventricular contractions from premature atrial contractions;
    sensing ventricular R-waves;
    computing a morphology metric of an R-wave and a corresponding preceding morphology metric of an immediately preceding R-wave;
    comparing one of a difference and a ratio of the R-wave morphology metric and the preceding R-wave morphology metric to the detection threshold;
    detecting a premature ventricular contraction in response to the comparison meeting the detection threshold requirement; and
    computing a measurement of the sensed ventricular R-waves in response to detecting the premature ventricular contraction.

2. The method of claim 1, further comprising:
    measuring intervals between consecutive R-waves;
    detecting a premature coupling interval; and
    computing the R-wave morphology metric and the preceding R-wave morphology metric in response to detecting the premature coupling interval.

3. The method of claim 1, wherein computing the morphology metric comprises:
    identifying a fiducial point along the R-wave;
    establishing a first time interval ending at the fiducial point;
    establishing a second time interval beginning at the fiducial point; and
    computing a first area over the first time interval and a second area over the second time interval.

4. The method of claim 3, wherein the first time interval has a first length and the second time interval has a second length different than the first length.

5. The method of claim 4, wherein the morphology metric is a sum of the first area and the second area.

6. The method of claim 1, wherein computing the morphology metric comprises determining a ratio of an amplitude of the R-wave and an amplitude of the preceding R-wave;
    determining a ratio of an area of the R-wave and an area of the preceding R-wave;
    and computing a weighted sum of the ratio of amplitudes and the ratio of areas.

7. The method of claim 6, wherein the amplitude ratio is a ratio of a maximum peak amplitude of the R-wave and a maximum peak amplitude of the preceding R-wave; and
    the area ratio is a ratio of a summed area of the R-wave and a summed area of the preceding R-wave, the summed area being a sum of a first area computed over a first time interval extending earlier than an R-wave fiducial point and a second area computed over a second time interval extending later than the R-wave fiducial point.

8. The method of claim 1, wherein establishing the detection threshold requirement comprises:
    computing a plurality of morphology metrics comprising at least one ratio of a morphology metric of an R-wave and a corresponding preceding morphology metric of a preceding R-wave;
    computing a threshold for each of the plurality of morphology metrics corresponding to a maximized confidence statistic for discriminating a premature ventricular contraction from a premature atrial contraction;
    comparing the maximized confidence statistic for each of the plurality of morphology metrics; and
    selecting a morphology metric and corresponding detection threshold requirement in response to the comparison of maximized confidence statistics.

9. The method of claim 8, wherein comparing the confidence statistic further comprises:
    establishing a performance score point value system;
    computing a plurality of statistical measures of discriminating premature ventricular contractions from premature atrial contractions for each of the thresholds computed for the plurality of morphology metrics;
    assigning points to each morphology metric threshold in response to the plurality of statistical measures according to the point value system; and
    summing the points assigned to a morphology metric to obtain a performance score for each of the morphology metrics;
    wherein selecting a morphology metric and corresponding detection threshold comprises selecting the metric and corresponding threshold having the highest performance score.

10. The method of claim 9 wherein the plurality of statistical measures comprise a confidence test statistic and at least one of a sensitivity measure, a specificity measure, a positive predictive measure and a negative predictive measure.

11. The method of claim 9 wherein establishing the detection threshold requirement further comprises computing a weighted sum of a first ratio of a first morphology metric and a first preceding morphology metric and second ratio of a second morphology metric and a second preceding morphology metric; and
    computing a detection threshold as a weighted sum of a first threshold determined for the first ratio based on a computed performance score and a second threshold determined for the second ratio based on a computed performance score.

12. The method of claim 1, wherein computing the measurement of the sensed ventricular R-waves comprises computing a heart rate turbulence measurement.

13. A medical device system for monitoring a cardiac signal in a patient, comprising:
at least one electrode pair for sensing ventricular R-waves; and
a processor configured to establish a detection threshold requirement for discriminating premature ventricular contractions from premature atrial contractions, compute a morphology metric of an R-wave and a corresponding preceding morphology metric of a preceding R-wave, compare one of a difference and a ratio of the R-wave morphology metric and the preceding R-wave morphology metric to the detection threshold, detect a premature ventricular contraction in response to the comparison meeting the detection threshold requirement, and compute a measurement of the sensed ventricular R-waves in response to detecting the premature ventricular contraction.

14. The system of claim 13, wherein the processor is further configured to:
measure intervals between consecutive R-waves;
detect a premature coupling interval; and
compute the R-wave morphology metric and the preceding R-wave morphology metric in response to detecting the premature coupling interval.

15. The system of claim 13 wherein computing the morphology metric comprises:
identifying a fiducial point along the R-wave;
establishing a first time interval ending at the fiducial point;
establishing a second time interval beginning at the fiducial point; and
computing a first area over the first time interval and a second area over the second time interval.

16. The system of claim 15, wherein the first time interval has a first length and the second time interval has a second length different than the first length.

17. The system of claim 16 wherein the morphology metric is a sum of the first area and the second area.

18. The system of claim 13 wherein computing the morphology metric comprises determining a ratio of an amplitude of the R-wave and an amplitude of the preceding R-wave;
determining a ratio of an area of the R-wave and an area of the preceding R-wave; and
computing a weighted sum of the ratio of amplitudes and the ratio of areas.

19. The system of claim 18 wherein the amplitude ratio is a ratio of a maximum peak amplitude of the R-wave and a maximum peak amplitude of the preceding R-wave;
the area ratio is a ratio of a summed area of the R-wave and a summed area of the preceding R-wave, the summed area being a sum of a first area computed over a first time interval extending earlier than an R-wave fiducial point and a second area computed over a time interval extending later than the R-wave fiducial point.

20. The system of claim 13 wherein establishing the detection threshold comprises:
computing a plurality of morphology metrics comprising at least one ratio of a morphology metric of an R-wave and a corresponding morphology metric of a preceding R-wave;
computing a threshold for each of the plurality of morphology metrics corresponding to a maximized confidence statistic for discriminating a premature ventricular contraction from a premature atrial contraction;
comparing the maximized confidence statistic for each of the plurality of morphology metrics; and
selecting a morphology metric and corresponding detection threshold in response to the comparison of maximized confidence statistics.

21. The system of claim 20 wherein comparing the confidence statistic further comprises:
establishing a performance score point value system;
computing a plurality of statistical measures of discriminating premature ventricular contractions from premature atrial contractions for each of the thresholds computed for the plurality of morphology metrics;
assigning points to each morphology metric threshold in response to the plurality of statistical measures and according to the point value system; and
summing the points assigned to a morphology metric to obtain a performance score for each of the morphology metrics;
wherein selecting a morphology metric and corresponding detection threshold comprises selecting the metric and corresponding threshold having the highest performance score.

22. The system of claim 19 wherein the plurality of statistical measures comprises a confidence test statistic and at least one of a sensitivity measure, a specificity measure, a positive predictive measure and a negative predictive measure.

23. The system of claim 21 wherein establishing the detection threshold requirement further comprises computing a weighted sum of a first ratio of a first morphology metric and a first preceding morphology metric and second ratio of a second morphology metric and a second preceding morphology metric; and
computing a detection threshold as a weighted sum of a first threshold determined for the first ratio based on a computed performance score and a second threshold determined for the second ratio based on a computed performance score.

24. The system of claim 13, wherein computing the measurement of the sensed ventricular R-waves comprises computing a heart rate turbulence measurement.

* * * * *